Jan. 11, 1949. C. E. KERN Plant Pat. 820
MAGNOLIA PLANT
Filed May 31, 1947
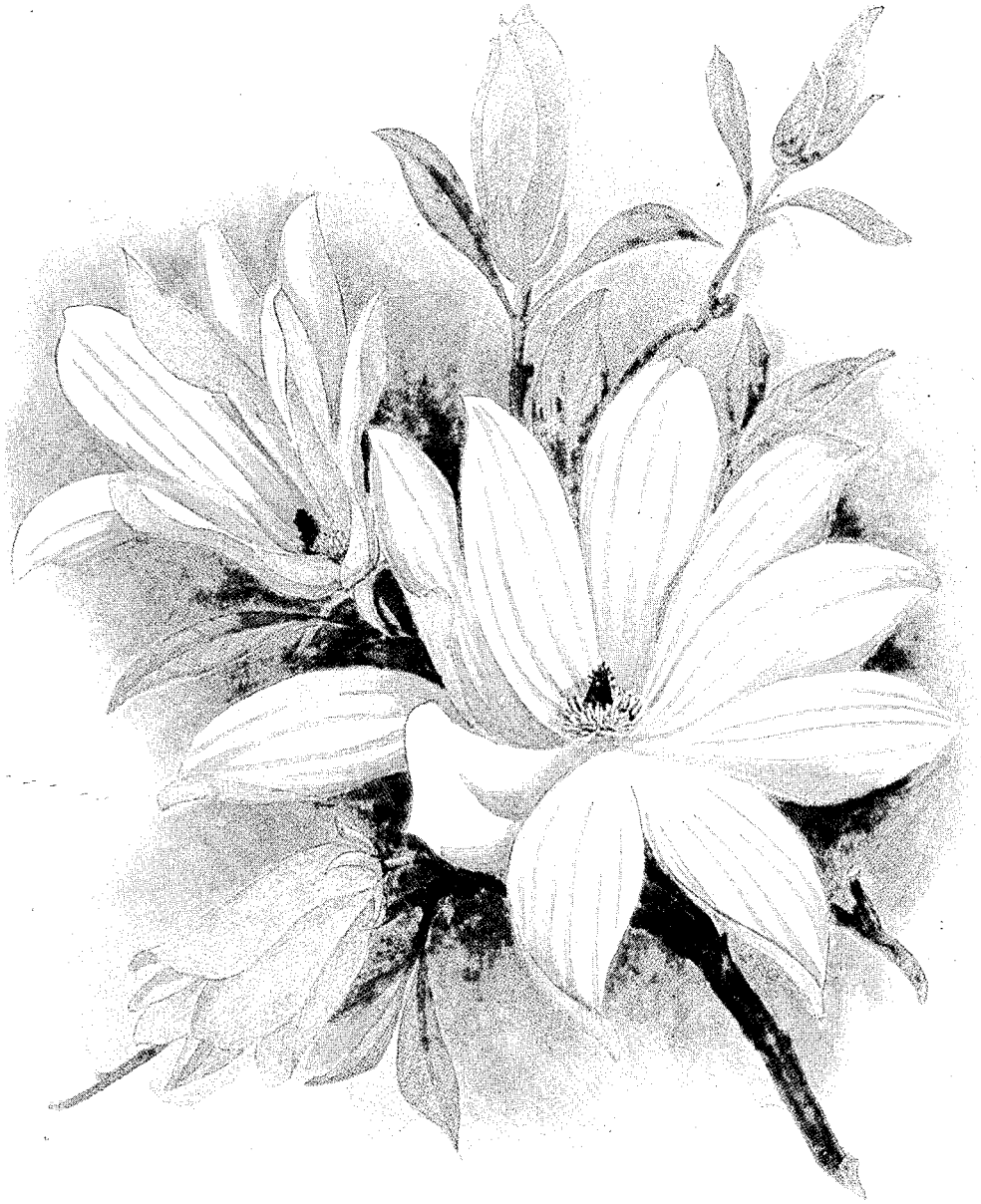
WITNESS
Addison J. Avery
INVENTOR
CARL EDWARD KERN,
by Rummler Rummler & Snow,
ATTYS.

Patented Jan. 11, 1949

Plant Pat. 820

UNITED STATES PATENT OFFICE

820

MAGNOLIA PLANT

Carl Edward Kern, Wyoming, Ohio

Application May 31, 1947, Serial No. 751,578

1 Claim. (Cl. 47—60)

The new and distinct variety of *Magnolia stellata* shrub herein described and illustrated is a cross between *Magnolia stellata* and an unnamed seedling, and is the result of definite breeding efforts carried on by me since 1935, in the vicinity of Cincinnati, Ohio. This new variety has been reproduced by grafting through several generations and its characteristics appear to be permanently fixed.

The primary object in carrying out this invention was to fix the deep rose pink coloring of the flowers, the compact upright growth, unusual abundance of bloom, lateness of season of blooming and the general hardiness of the plant.

This new variety of plant in wood and growth habit resembles *Magnolia stellata,* but the bloom is distinctly different. It is intermediate in form between *Magnolia stellata* and *Magnolia soulangeana* types, with broader flower petals than *Magnolia stellata,* the flowers of the latter being pure white in coloring.

The accompanying illustration shows the blooms in various stages of development.

Referring to the novel characteristics of this new variety, the flower is a large double blossom of rich deep rose pink coloring on the outer surface of the petals and on the inner surface a warm white suffused with a delicate shade of pink at the tips. In contrast to this the tightly furled buds are a deep reddish-purple with three small green sepals at the base. As this shrub has an excellent long blooming season, there are simultaneously present the three stages of bloom-coloring—the brownish-lavender buds enclosed in the stipular spathe; the reddish-purple bud petals when the spathe has fallen; and the open flowers with their harmonious combination of colors, of the white open face with the showy cluster of stamens, and rose-pink under-coloring; combining to make this shrub conspicuous and distinctive.

The following is an itemized description in schedule form of the new variety:

Parentage: Seedling. Seed parent—*Magnolia stellata* X, unnamed seedling.

*Plant*

Size: 6 to 8 feet high.
Shape: Upright.
Hardy: Yes.
Regular bearer: Yes.
Trunk: Smooth and stocky.
Branches: Smooth. Color—New wood, reddish-brown; old wood, light gray.
Lenticels:
*Number.*—17 per square inch approximately.
*Size.*—1 mm.

Leaves:
*Length.*—5 inches.
*Width.*—2½ inches.
*Shape.*—Spathulate.
*Color.*—Upper side—dark green; Under side—lighter green.
*Edges.*—Smooth.
*Petiole.*—Length—½ inch.

*Flower*

Hardy.
Color: Deep rose pink outer surface; inner surface—white.
Texture: Substantial and velvety.
Pubescence: Smooth.
Borne: Singly.
Form: Vase-shaped.
Petalage: 8 to 10 in number.
Size: 3 inches in length.
Date of bloom: Late April.
Stems: ⅜ inch to ½ inch.
Lasting qualities of flowers: Excellent; long blooming season.
Resistance to disease: Very resistant.

There is no fruit.

The color designations according to "A Dictionary of Color by Maerz and Paul," are as follows:

| | Section | Plate | Letter | No. |
|---|---|---|---|---|
| 1 | Inner surface a warm white | 1 | A | 1 |
| 2 | Shading into | 1 | B | 1 |
| 3 | Faint suffused pale pink at edges in narrow band | 1 | A | 3 |
| 4 | Back of petal lightest shade | 41 | I | 3 |
| 5 | Shading into base of petals | 41 | J | 5 |
| 6 | Large buds | 43 | J | 4 |
| 7 | Shading into | 43 | L | 4 |
| 8 | Small buds | 44 | L | 5 |
| 9 | Leaf (body color) | 22 | L | 6 |
| 10 | Stem or branch (old wood) | 15 | A | 2 |

The plant is especially characterized by its unusual abundance and rich coloring of bloom, its compact upright growth, general hardiness, and late blooming season.

Having thus disclosed my invention, I claim:

A new and distinct variety of *Magnolia stellata* plant substantially as shown and described, characterized particularly by its floriferousness, the coloring of its blooms, its compact upright growth, the lateness and length of its blooming season, and its healthy, vigorous growth.

CARL EDWARD KERN.

No references cited.